United States Patent [19]

Sommer et al.

[11] 4,216,163
[45] Aug. 5, 1980

[54] N-SULFO ALKANE AMINO ALKANE PHOSPHORIC ACIDS AND THEIR ALKALI METAL SALTS, AND A PROCESS OF PRODUCING SAME

[75] Inventors: Klaus Sommer, Heidelberg; Hermann Weber, Hemsbach, both of Fed. Rep. of Germany

[73] Assignee: Benckiser-Knapsack GmbH, Ladenburg, Fed. Rep. of Germany

[21] Appl. No.: 891,043

[22] Filed: Mar. 28, 1978

[30] Foreign Application Priority Data

Mar. 29, 1977 [DE] Fed. Rep. of Germany ....... 2713827
Apr. 14, 1977 [DE] Fed. Rep. of Germany ....... 2716417

[51] Int. Cl.$^2$ .......................... C07F 9/38; C14C 9/00; D06M 1/00; C02B 5/06
[52] U.S. Cl. .................................... 260/502.5; 210/58; 252/8.57; 252/8.8; 252/180; 252/181
[58] Field of Search ...................................... 260/502.5

[56] References Cited

U.S. PATENT DOCUMENTS

| | | | |
|---|---|---|---|
| 2,599,807 | 6/1952 | Bersworth | 260/502.5 |
| 2,673,213 | 3/1954 | Bersworth | 260/502.5 |
| 2,836,620 | 5/1958 | Bersworth et al. | 260/502.5 |
| 2,917,528 | 12/1959 | Ramsey et al. | 260/502.5 |
| 3,160,632 | 12/1964 | Toy et al. | 260/502.5 |
| 4,006,182 | 2/1977 | Ploger et al. | 260/502.5 |
| 4,051,175 | 9/1977 | Andrew et al. | 260/502.5 |
| 4,085,134 | 4/1978 | Redmore et al. | 260/502.5 |

FOREIGN PATENT DOCUMENTS 513981 10/1976 U.S.S.R. ............................... 260/502.5

*Primary Examiner*—Joseph E. Evans
*Attorney, Agent, or Firm*—Schwartz, Jeffery, Schwaab, Mack, Blumenthal & Koch

[57] ABSTRACT

Novel and highly advantageous N-sulfo alkane amino alkane phosphonic acids and their alkali metal salts are provided. Said phosphonic acids are produced by reacting an alkali metal salt of an amino phosphonic acid with a halo, preferably chloro, or hydroxy alkane sulfonic acid or their alkali metal salts in an alkaline medium, while heating.

In place of the halo and especially chloro or hydroxy alkane sulfonic acid reactants, there can also be used compounds which are capable of producing hydroxy alkane sulfonates such as carbylsulfate or aldehydes or, respectively, ethylene oxide with alkali metal bisulfites or metasulfites. The reaction is preferably carried out in a molar proportion of about 1:1 to about 1:2. The novel compounds are excellent complexing or sequestering agents especially with respect to polyvalent metal ions. They are highly resistant against hydrolysis and high temperatures and are of a very high water solubility.

10 Claims, No Drawings

N-SULFO ALKANE AMINO ALKANE PHOSPHORIC ACIDS AND THEIR ALKALI METAL SALTS, AND A PROCESS OF PRODUCING SAME

BACKGROUND OF THE INVENTION (1) Field of the Invention

The present invention is concerned with N-sulfo alkane amino alkane phosphonic acids and their alkali metal salts as well as with a process of producing such phosphonic acids and their salts, with a method of using said compounds, and with useful compositions comprising the same.

(2) Description of the Prior Art

N-Carboxy alkyl amino alkane diphosphonic acids and N-carboxy methyl amino aryl alkane diphosphonic acids are described in German Pat. No. 2,318,416.

British Pat. No. 1,142,294 discloses carboxy amino alkane phosphonic acids which are characterized by the group $>N-CH_2PO_3H_2$. Said compounds are obtained, for instance, by reacting amino acetic acid with formaldehyde and phosphorus trichloride in the presence of water.

The N-carboxy alkyl amino alkane diphosphonic acids disclosed in German Pat. No. 2,318,416 are produced by reacting amino alkane di- or, respectively, triphosphonic acids in an alkaline medium with formaldehyde and an alkali metal cyanide at a specific molecular proportion while heating.

SUMMARY OF THE INVENTION

It is one object of the present invention to provide novel and highly advantageous N-sulfo alkane amino alkane phosphonic acids and their alkali metal salts.

Another object of the present invention is to provide a simple and effective process of producing said novel N-sulfo alkane amino alkane phosphonic acids and their alkali metal salts.

A further object of the present invention is to provide a method of using said novel N-sulfo alkane amino alkane phosphonic acids and their alkali metal salts as sequestering agents which form complex compounds with divalent and polyvalent metal ions so that they are useful in all instances in which effective complex-forming ability is required.

Still another object of the present invention is to provide compositions which, due to their complexing or sequestering ability can be used as agents for decreasing the hardness of aqueous systems or for eliminating deleterious or obnoxious effects of polyvalent metal ions, for instance, for softening hard water, as additives to textile treatment baths, in the manufacture of paper, in tanning baths, and for other purposes.

Another object of the present invention is to stabilize the hardness of aqueous media when adding thereto the novel N-sulfo alkane amino alkane phosphonic acids or their alkali metal salts in substoichiometric amounts, i.e. as agents in carrying out the so-called "threshold process".

In principle, the novel and advantageous N-sulfo alkane amino alkane phosphonic acids according to the present invention correspond to the following formula:

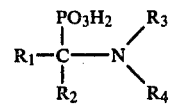

in which $R_1$ indicates hydrogen, alkyl with 1 to 11 carbon atoms, especially ethyl and methyl, aryl, especially phenyl, tolyl, and chloro phenyl, aralkyl, especially benzyl, cycloalkyl, especially cyclohexyl, amino alkylene with 2 to 5 carbon atoms, especially amino methylene, or the lower alkylene phosphonic acid group, especially the ethylene phosphonic acid group;

$R_2$ indicates hydrogen or the phosphonic acid group $PO_3H_2$;

$R_3$ indicates the alkane sulfonic acid group $C_nH_{2n}SO_3H$ or a lower alkylene phosphonic acid group, especially the methylene phosphonic acid group $CH_2PO_3H_2$; and $R_4$ indicates hydrogen, provided $R_3$ is not the lower alkylene phosphonic acid group, or an alkylene sulfonic acid group $C_nH_{2n}SO_3H$; whereby n of $R_3$ and $R_4$ indicates one of the numerals 1 to 11.

The hydrogen atoms of the acidic groups can be replaced in said phosphonic acid compounds by alkali metal, such as sodium or potassium.

The novel N-sulfo alkane amino alkane phosphonic acids according to the present invention differ from heretofore known phosphonic acids by having at least one of the hydrogen atoms attached to the nitrogen atom replaced by an alkane sulfonic acid group.

To produce the N-sulfo alkane amino alkane phosphonic acids according to the present invention, alkali metal salts of amino phosphonic acids of the formula

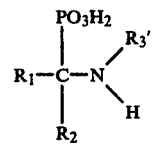

in which $R_1$ indicates hydrogen, alkyl with 1 to 11 carbon atoms, especially ethyl and methyl, aryl, especially phenyl, tolyl, and chloro phenyl, aralkyl, especially benzyl, cycloalkyl, especially cyclohexyl, amino alkylene with 2 to 5 carbon atoms, especially amino methylene, or the lower alkylene phosphonic acid group, especially the ethylene phosphonic acid group;

$R_2$ indicates hydrogen or the phosphonic acid group; and $R_3'$ indicates hydrogen or a lower alkylene phosphonic acid group, especially the methylene phosphonic acid group, are reacted in an alkaline medium, while heating, with an alkali metal salt of a halo alkane sulfonic acid and more particularly of a chloro alkane sulfonic acid of the formula $Hal.C_nH_{2n}SO_3H$ or of a hydroxy alkane sulfonic acid of the formula $HOC_nH_{2n}SO_3H$. In said formula n is one of the numerals 1 to 11. The reactants are reacted in the molar proportion between about 1:1 and about 1:2 of phosphonic acid to sulfonic acid at a pH-value of at least 9.0 and preferably between about 10.0 and about 11.0 and at a higher temperature between about 20° C. and 250° C., preferably at elevated temperature, especially at a temperature between about 60° C. and about 220° C.

Halo alkane sulfonates and more particularly chloro alkane sulfonates are preferably reacted at a temperature around 100° C. while hydroxy methane sulfonates enter noticeably into reaction with the amino phosphates already at a temperature of about 60° C. The reaction with higher 1-hydroxy alkane-1-sulfonates, such as, for instance, with 1-hydroxy ethane-1-sulfonates takes place at a somewhat slower rate. In contrast thereto it has been found that it is necessary, when using 2-hydroxy ethane-1-sulfonates, to carry out the reaction at a temperature between about 180° C. and about 240° C. under pressure.

The preferred chloro sulfonates used in this reaction are the sodium or, respectively, potassium salts of the following compounds:
1-chloro ethane-2-sulfonic acid,
1-chloro propane-2-sulfonic acid,
1-chloro propane-3-sulfonic acid,
2-chloro butane-4-sulfonic acid,
1-chloro butane-4-sulfonic acid,
1-chloro octane-2-sulfonic acid,
3-chloro undecane-1-sulfonic acid.

The preferred hydroxy alkane sulfonates to be used in this reaction are the sodium or, respectively, potassium salts of the following compounds:
Hydroxy methane sulfonic acid,
1-hydroxy ethane-1-sulfonic acid,
2-hydroxy ethane-1-sulfonic acid,
1,2-dihydroxy ethane-1,2-disulfonic acid,
hydroxy carboxy methane sulfonic acid.

Suitable phosphonic acid reactants are all amino alkane phosphonic acids which contain at the amino group at least one hydrogen atom that can be substituted, and which are characterized by the formula given hereinabove.

On reacting the alkali metal salts of the chloro alkane sulfonic acids, there are obtained mono- or di-substituted sulfo alkane amino alkane di- or triphosphonic acids depending upon the molar proportion selected for the reaction.

When using as the one reactant a 2-hydroxy ethane-1-sulfonate, there are obtained on reaction with amino alkane phosphonic acids only compounds which carry one sulfo alkane group at the nitrogen atom.

In place of the 1-hydroxy alkane-1-sulfonates, there can also be used as reactants the corresponding aldehydes or, respectively, acetals together with water soluble sulfites or bisulfites and preferably with alkali metal sulfites or bisulfites.

In place of the 2-hydroxy ethane-1-sulfonates there can be used the starting materials which are employed for producing said hydroxy ethane sulfonic acid. Said starting materials are directly reacted with the corresponding phosphonates. In this manner it is possible to react carbyl sulfate which has been neutralized with alkali metal hydroxides or carbonates before the reaction, with amino alkane phosphonic acids in an alkaline medium. Thereby, the corresponding N-sulfo alkane amino alkane phosphonic acids are produced according to the following equation:

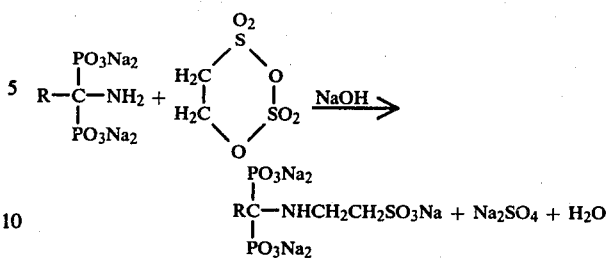

Actual sulfo alkylation takes place in this case at a temperature between about 180° C. and about 240° C. under pressure.

Another possibility of producing the N-sulfo alkane amino alkane phosphonic acids according to the present invention comprises the process of reacting mixtures of ethylene oxide and sodium bisulfite which can also be used for producing the hydroxy ethane sulfonic acids, as such with amino phosphonic acids. In this case, the amino phosphonic acid is preferably mixed with the sodium bisulfite solution, and the ethylene oxide is subsequently introduced or added drop by drop thereto. In this reaction it is of crucial importance for the reaction to take place, that the reactants are added in the above-given order because oxiranes can react with sodium bisulfite as well as with the amino group to amino alkane phosphates. Thus, when changing the order of addition of the reactants, predominantly N-hydroxy alkane amino alkane phosphonic acids are produced. However, when proceeding in the above-given order of addition, said hydroxy alkane derivatives are formed only in minor amounts.

When using ethylene oxide and sodium bisulfite as reactants, the reaction is also carried out at a temperature between about 180° C. and about 240° C. according to the following equation:

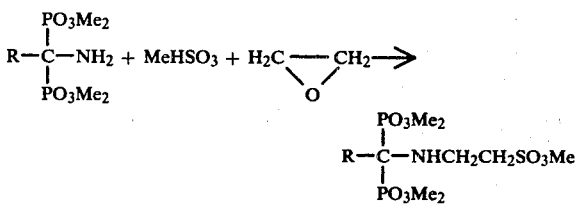

The novel phosphonic acids according to the present invention are distinguished over similar known phosphonic acids by the feature that they can readily be produced in a good yield and that their water solubility is excellent with regard to most of the uses they are employed for. They are satisfactory complexing or sequestering agents with respect to bivalent or polyvalent metal ions. They can be employed with advantage in all those instances in which a good complexing or sequestering power is required. More particularly it is to be pointed out that they are highly resistant to hydrolysis even at high temperatures. Thus they can be used in all those instances in which temperatures exceeding 100° C. are encountered. Due thereto they can be employed in all aqueous media in which the hardness causing agents present therein cause trouble or in which the effect of polyvalent metal ions is to be excluded. More in particular, they have proved to be useful for softening hard water, as additive to textile treatment baths, in the paper manufacture, and in tanning baths.

The novel phosphonic acids are also useful for stabilizing the hardness of water when added in substoichiometric amounts, i.e. for carrying out the so-called "threshold processes".

More particularly there is to be mentioned the remarkably good solubility of the free acids in aqueous media. Most of the heretofore known amino phosphonic acids do not exhibit such a high water solubility. Thus the compounds described hereinafter in the examples are soluble at least in amounts of 100 g./100 cc.

DESCRIPTION OF THE PREFERRED EMBODIMENTS

The following examples serve to illustrate the present invention without, however, being limited thereto.

EXAMPLE 1

47.8 g. of amino methane diphosphonic acid and 50 g. of sodium hydroxide are dissolved in 300 cc. of water. A solution of 42 g. of sodium chloro ethane sulfonate in 150 cc. of water is added drop by drop at a temperature between 30° and 50° C. to said solution, while stirring. The mixture is boiled for one hour while continuing vigorous stirring. After cooling the reaction mixture is weakly acidified by the addition of dilute hydrochloric acid. Any precipitated non-reacted amino methane diphosphonic acid is filtered off. The solution is treated sulfo phosphonic acid. After concentrating the solution by evaporation, methanol or ethanol are added thereto in order to cause crystallization of the reaction product. The resulting N-sulfo ethane amino methane diphosphonic acid has a calcium binding power of 22.8 g. Ca/100 g. at a pH of 10.0. Yield: 92% of the theoretical yield.

Analysis: Found: C: 12.4%, N: 4.6%, P: 19.8%, S: 11.1%. Calculated: C: 12.04%, N: 4.68%, P: 20.71%, S: 10.72%.

EXAMPLE 2

A solution of the sodium salt of amino methane diphosphonic acid is added to a solution of 90 g. of sodium chloro ethane sulfonate and 250 cc. of water, while stirring. The solution of the sodium salt of amino methane diphosphonic acid was prepared by dissolving 47.8 g. of amino methane diphosphonic acid and 60 g. of sodium hydroxide in 300 cc. of water. After the addition of the amino methane diphosphonate solution the reaction mixture is boiled under reflux for 30 minutes. The resulting reaction solution is treated with a cation-exchange agent. The thus treated solution is evaporated to dryness. The N,N-bis-sulfo ethane amino methane diphosphonic acid is obtained as a colorless oil. Yield: 84%.

Analysis: Found: N: 3.6%, P: 14.9%, S: 15.8%. Calculated: N: 3.44%, P: 15.21%, S: 15.75%.

EXAMPLE 3

50 g. of 1-amino ethane-1,1-diphosphonic acid and 40 g. of chloro ethane sulfonic acid are suspended in 200 cc. of water. 240 g. of a 30% potassium hydroxide solution are added drop by drop thereto, while stirring vigorously. The reaction mixture is subsequently boiled under reflux for one more hour. In order to produce the free N-sulfo ethane-1-amino ethane-1,1-diphosphonic acid, the reaction solution is treated with a cation-exchange agent as described in the preceding examples. The resulting solution is concentrated by evaporation, and the oily residue is washed by suspending it in methanol or ethanol. Yield: 89%.

Analysis of the dried residue: Found: C: 15.2%, N: 4.6%, P: 19.4%, S: 10.9%. Calculated: C: 15.34%, N: 4.47%, P: 19.78%, S: 10.22%.

EXAMPLE 4

50 g. of 1-amino ethane-1,1-diphosphonic acid and 70 g. of potassium hydroxide are dissolved in 200 cc. of water. 54 g. of potassium chloro butane sulfonate dissolved in 80 cc. of water are added drop by drop thereto at a temperature between 40° C. and 50° C., while stirring. After said addition is completed, boiling of the reaction mixture is continued for one and a half hours. The reaction solution is weakly acidified and treated with an acid exchange agent in order to yield the N-sulfo butane-1-amino ethane-1,1-diphosphonic acid. The reaction product is dried. Yield: 83%.

Analysis: Found: N: 4.2%, P: 17.8%, S: 9.8%. Calculated: N: 4.11%, P: 18.16%, S: 9.39%.

EXAMPLE 5

The tetra-sodium or, respectively, tetra-potassium salt of 1-amino ethane-1,1-diphosphonic acid is prepared as described hereinabove from 50 g. of 1-amino ethane-1,1-diphosphonic acid, and 50 g. of sodium hydroxide or the corresponding amount of potassium hydroxide. Said salts are reacted in the same manner, as described in the preceding examples, with the sodium salt or the potassium salt of 1-chloro octane-2-sulfonic acid. After removing the alkali metal ions by means of a cation-exchange agent and evaporating the resulting solution to dryness in a water jet vacuum, N-sulfo octane-1-amino ethane-1,1-diphosphonic acid is obtained. Yield: 72%.

Analysis: Found: N: 3.6%, P: 15.7%, S: 8.3%. Calculated: N: 3.52%, P: 15.61%, S: 8.05%.

EXAMPLE 6

66 g. of phenyl amino methane diphosphonic acid and 48 g. of potassium chloro ethane sulfonate are suspended in 200 cc. of water. 70 g. of potassium hydroxide in 100 cc. of water are allowed to flow into said suspension, while continuing stirring. After boiling the reaction mixture under reflux for one hour, the resulting solution is passed through a cation-exchange agent in order to remove the alkali metal ions and the potassium chloride formed during reaction as described hereinabove, and is then concentrated by evaporation. Yield: 85%.

Analysis: Found: N: 3.8%, P: 16.2%, S: 8.9%. Calculated: N: 3.74%, P: 16.55%, S: 8.57%.

EXAMPLE 7

75 g. of 1-amino propane-1,1,3-triphosphonic acid, 48 g. of sodium chloro ethane sulfonate, and 70 g. of sodium hydroxide are dissolved in 350 cc. of water. The resulting solution is boiled for two hours. After cooling and treating the same with a cation-exchange agent, a solution of N-sulfo ethane-1-amino propane-1,1,3-triphosphonic acid is obtained and is concentrated by evaporation. Yield: 94%.

Analysis: Found: N: 3.6%, P: 22.4%, S: 7.4%. Calculated: N: 3.44%, P: 22.82%, S, 7.88%.

EXAMPLE 8

55 g. of 1-amino propane-1,1-diphosphonic acid and 48 g. of sodium chloro propane sulfonate are dissolved in 400 cc. of water. 100 g. of a 50% sodium hydroxide solution are added thereto. The reaction mixture is boiled under reflux for one hour, whereafter the resulting solution is treated with a cation-exchange agent in order to yield the N-sulfo propane-1-amino propane-1,1-diphosphonic acid. The solution is then evaporated to dryness.

Analysis: Found: N: 4.4%, P: 18.0%, S: 9.6%. Calculated: N: 4.11%, P: 18.16%, S: 9.39%.

EXAMPLE 9

50 g. of imino-bis-methane phosphoric acid and 38 g. of chloro ethane sulfonic acid are dissolved in 400 cc. of water. 62 g. of sodium hydroxide are added to said solution. The reaction mixture is boiled for 45 minutes. The resulting solution is treated with a cation-exchange agent and concentrated by evaporation.

Analysis: Found: C: 15.0%, N: 4.5%, P: 19.9%, S: 10.0%. Calculated: C: 15.34%, N: 4.47%, P: 19.78%, S: 10.22%.

EXAMPLE 10

A solution of 48 g. of amino methane diphosphonic acid, 56 g. of potassium hydroxide, and 39 g. of the potassium salt of hydroxy methane sulfonic acid in 300 cc. of water is stirred at 70° to 75° C. for three hours. In order to produce a crystalline salt, methanol is carefully added to the reaction solution and the mixture is allowed to stand for some time. The resulting crystals are dried at 80° C. in a vacuum.

EXAMPLE 11

27 g. of 1,2-diamino ethane-1,1-diphosphonic acid are dissolved in 125 cc. of 2 N potassium hydroxide solution. 38 g. of the potassium salt of 1,2-dihydroxy ethane-1,2-disulfonic acid are added thereto and the reaction mixture is kept at 70° to 80° C. for two hours. The resulting reaction solution is evaporated in a vacuum to half its volume and methanol is added thereto. On allowing the mixture to stand, a crystalline product is obtained which is dried in a vacuum at 50° C.

Analysis: Found: K: 26.8%, C: 8.8%, N: 5.2%, P: 10.5%, S: 11.9%.

EXAMPLE 12

50 g. of 1-amino ethane-1,1-diphosphonic acid and 43 g. of potassium hydroxide are dissolved in 300 cc. of water. 28 g. of potassium bisulfite and 8 g. of trioxane are added portion by portion to said solution. The reaction mixture is then heated at 50° C. for two hours. Thereafter, it was not possible to detect any amino ethane diphosphonic acid in the thin-layer chromatogram.

EXAMPLE 13

53 g. of 1-amino propane-1,1-diphosphonic acid are heated with 30 g. of a 30% formaldehyde solution and with 180 cc. of water at 80° C. for 30 minutes. After allowing the mixture to cool, a solution of 28 g. potassium metabisulfite in 375 cc. of a 2 N potassium hydroxide solution is added drop by drop thereto. The reaction mixture is kept at 65° C. for one hour.

EXAMPLE 14

25.6 g. of imino bis-methane phosphonic acid are mixed with 190 cc. of a 2 N sodium hydroxide solution and 20 g. of the monohydrate of the sodium salt of hydroxy methane sulfonic acid in 100 cc. of water and the mixture is kept at 60° to 70° C. for two hours. After cooling, methanol is added and the sodium salt of nitrilo sulfo methane bis-methane phosphonic acid is precipitated. Yield: 87%.

EXAMPLE 15

The solution of the tetra-potassium salt of 48 g. of amino methane diphosphonic acid and 45 g. of the potassium salt of 2-hydroxy ethane-1-sulfonic acid (potassium isethionate) in 200 cc. of water is heated in an autoclave at a temperature of 190° to 230° C. for five to six hours. After cooling, the resulting solution is slightly acidified by the addition of dilute hydrochloric acid, treated with a cation-exchange agent, and concentrated by evaporation in a water jet vacuum. After washing the residue with ethanol, the N-sulfo ethane amino methane diphosphonic acid is obtained in the form of a colorless oil.

Analysis: Found: C: 12.2%, N: 4.5%, P: 20.0%, S: 11.0%. Calculated: C: 12.04%, N: 4.68%, P: 20.71%, S: 10.72%.

EXAMPLE 16

Reaction of 51 g. of 1-amino ethane-1,1-diphosphonic acid and 40 g. of sodium hydroxide or, respectively, 56 g. of potassium hydroxide with 40 g. of sodium isethionate yields 64 g. of N-sulfo ethane-1-amino ethane-1,1-diphosphonic acid.

Analysis: Found: C: 15.7%, N: 4.6%, P: 20.0%, S: 10.1%. Calculated: C: 15.34%, N: 4.47%, P: 19.78%, S: 10.22%.

EXAMPLE 17

55 g. of 1-amino propane-1,1-diphosphonic acid, 40 g. of sodium hydroxide, and 40 g. of the sodium salt of 2-hydroxy ethane-1-sulfonate (sodium isethionate) in 400 cc of water are reacted at 200° to 220° C. under pressure and the reaction mixture is treated with a cation-exchange agent. 62 g. of N-sulfo ethane-1-amino propane-1,1-diphosphonic acid are obtained.

Analysis: Found: N: 4.1%, P: 19.5%, S: 9.4%. Calculated: N: 4.28%, P: 18.96%, S: 9.79%.

EXAMPLE 18

Reaction of 67 g. of phenyl amino methane diphosphonic acid, 40 g. of sodium hydroxide, and 40 g. of sodium isethionate in 250 cc. of water as described hereinabove in example 15, yields N-sulfo ethane phenyl amino methane diphosphonic acid. Yield: 74%.

Analysis: Found: N: 3.9%, P: 16.9%, S: 8.3%. Calculated: N: 3.74%, P: 16.55%, S: 8.56%.

EXAMPLE 19

Reaction of 51 g. of imino bis-methane phosphonic acid, 40 g. of sodium hydroxide, and 40 g. of sodium isethionate in 250 cc. of water yields 56 g. of N,N-bis-phosphono methane amino ethane sulfonic acid.

Analysis: Found: C: 15.1%, N: 4.4%, P: 19.9%, S: 10.5%. Calculated: C: 15.34%, N: 4.47%, P: 19.78%, S: 10.22%.

Analysis and Rf-values of the thin-layer chromatogram correspond to that of the product which is obtained on phosphono methylation of taurine by means of phosphorous acid and formaldehyde.

EXAMPLE 20

75 g. of 1-amino propane-1,1,3-triphosphonic acid, 84 g. of potassium hydroxide, and 46 g. of the potassium salt of 2-hydroxy ethane-1-sulfonic acid are dissolved in 250 cc. of water. The solution is heated in a steel autoclave at a temperature of about 210° C. for 6 to 8 hours. In order to produce the free N-sulfo ethane-1-amino propane-1,1,3-triphosphonic acid, the resulting reaction solution is cooled, slightly acidified with dilute hydrochloric acid, treated with a cation-exchange agent, and concentrated by evaporation in a water jet vacuum. After washing the residue with methanol or ethanol, the free acid is obtained as a colorless oil which crystallizes on standing for a prolonged period of time. Yield: 72%.

Analysis: Found: C: 14.1%, N: 3.5%, P: 23.0%, S: 7.7%. Calculated: C: 14.75%, N: 3.44%, P: 22.82%, S: 7.87%.

Of course, many changes and variations in the reactants used, in the reaction conditions, duration, temperature, and pressure, in the manner in which the reaction solution is worked up, purified, and converted into the N-sulfo alkane amino alkane phosphonic acid according to the present invention, and the like are made by those skilled in the art in accordance with the principles set forth herein and in the claims annexed hereto.

Preferably strongly acid cation exchanging agents such as, for instance, sulfonated polymerization products of styrene, divinyl benzene and the like are used for producing the free sulfo alkane amino alkane phosphonic acids of the present invention.

The chloro ethane sulfonate used in Examples 1 to 3, 6, 7, and 9 is the sodium salt of 1-chloro ethane-2-sulfonic acid. In the other examples any of the known chloro propane sulfonates or chloro butane sulfonates may be used as one of the reactants.

The novel sulfo alkane amino alkane phosphonic acids and their alkali metal salts as well as their reaction solutions or the mother liquors obtained after separating the crystalline acids are used, as stated above, as additives to aqueous media to eliminate or suppress the disturbing and obnoxious effects of hardness-forming agents in said media or to exclude the action of polyvalent metal ions. On account of their high sequestering power they can advantageously be used for preventing scale and deposit formation in aqueous systems as they are employed, for instance, in textile bleaching baths, in water used for sterilizing cans, for preventing formation of resinous deposits in the manufacture of paper, and the like.

The following examples illustrate the manner in which the sulfo alkane amino alkane phosphonic acids according to the present invention can be employed without, however, limiting their usefulness to these examples.

EXAMPLE 21

15 g. of desized cotton fabric of a starting degree of whitness of 58.6, as determined with the "ELREPHO apparatus with filter R 46", and of a degree of polymerization value of 1842 are bleached with the compositions as given hereinafter in a laboratory equipment of the "Multicolor" type of the firm Pretema A.G. The proportion of fabric to bath was 1 to 20. Bleaching was effected at a temperature of 150° C. for 30 minutes (hot temperature process).

The composition of the bleaching baths was as follows:

Bleaching Bath A 5 cc./l. of 30% hydrogen peroxide, sodium hydroxide solution in an amount sufficient to adjust the pH-value of the bleaching bath to a pH of 12, 0.2 g/l. of N-(2-sulfo ethane)-1-amino ethane-1,1-diphosphonic acid.

Bleaching Bath B

The composition is the same as that of bleaching bath A but with the addition of 4 mg/l. of ferric ions to the aqueous bath.

Bleaching Bath C

The composition is the same as that of bleaching bath A but water of 5° German hardness (magnesium hardness) is used for making up the bleaching solution.

| | Bleaching Results | |
|---|---|---|
| | Degree of Polymerization | Degree of Whiteness |
| Bleaching Bath A | 1550 | 75.6 |
| Bleaching Bath B | 1410 | 72.2 |
| Bleaching Bath C | 1580 | 75.8 |

It is evident from these tests that the degree of whiteness is very considerably increased while the degree of polymerization is reduced by only about 14% to about 24% although bleaching is effected at the high temperature of 150° C.

EXAMPLE 22

The following test was carried out in an upright autoclave of a capacity of 10 liters of water. The autoclave was operated at about 4 atmospheres gauge and at a temperature of 140° C. The autoclave was charged with conventional tin plated cans.

Tap water of the following composition was used for sterilization:

| | |
|---|---|
| Total degree of hardness | 25° German hardness |
| Hardness due to carbonates | 17° German hardness |
| Chlorides | 53 mg./l. |
| Sulfates | 85 mg./l. |
| Free carbon dioxide | 40 mg./l. |
| Bound carbon dioxide | 125 mg./l. |
| pH-value | 7.2 |

Before sterilization of the cans 5 cc. of a 30% solution of N-(2-sulfo propane)-1-amino ethane-1,1-diphosphonic acid were added to the water. Addition of said phosphonic acid resulted in keeping not only the sterilized cans but also the autoclave free of incrustations. The cans had a glossy and shiny appearance.

EXAMPLE 23

250 g. of bleached sulfite pulp known for its property of causing continuously difficulty on the paper machine due to resin deposition were beaten to a 3% suspension in water. The resulting stock suspension was ground in a Hollander beater to about 78° Schopper-Riegler, i.e. so as to form a well beaten pulp suitable for producing dense sheets of parchment-like paper. The pH-value of the resulting slurry was 6.0. Before starting beating, 0.5 kg. of the tetrasodium salt of N-(2-sulfo ethane)-1-amino ethane-1,1-diphosphonic acid were added to the slurry in the Hollander beater. After beating and refining, 0.8 kg. of the same phosphonic acid were admixed thereto.

When proceeding in this manner, no resinous deposits were observed on the walls of the Hollander beater and also not on the pipe lines and subsequently on the paper machine.

EXAMPLE 24

Treatment of water used for sterilization of cans.

Tin plated cans are placed into a 10 liter autoclave. Tap water of the following composition is used for sterilization of the cans:

| Total hardness | 25° German hardness |
|---|---|
| Carbonate hardness | 17° German hardness |
| Chlorides | 53 mg./l. |
| Sulfates | 85 mg./l. |
| Free carbon dioxide | 40 mg./l. |
| Bound carbon dioxide | 125 mg./l. |
| pH-value | 7.2 |

5 cc. of N-(2-sulfo ethane)-1-amino ethane-1,1-diphosphonic acid are added to the tap water. Sterilization is effected by heating to 140° C. at about 4 atmospheres gauge. Addition of the phosphonic acid compound inhibits scale and deposit formation on the sterilized cans as well as on the walls of the autoclave.

The same or similar results as described in Examples 21 to 24 were observed when using other N-sulfo alkane amino alkane diphosphonic acids as obtained, for instance, according to Examples 1 to 20.

The phosphonic acids according to the present invention can be used as sequestering, complexing, and/or chelating agents for other purposes, for instance, as described in U.S. Pat. No. 3,860,391 in peroxide bleaching baths and U.S. Pat. Nos. 3,833,517 and 3,954,401 in baths for the treatment of cellulose fiber materials, and for other uses for which such agents have been used before. If desired, the alkali metal or ammonium salts or solutions thereof can also be used in place of the acids. These salts are prepared by neutralizing the phosphonic acids with the calculated amounts of alkali metal hydroxides or ammonia.

We claim:

1. An N-sulfo alkane amino alkane phosphonic acid of the formula

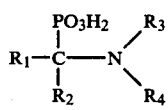

in which
  $R_1$ indicates hydrogen, alkyl with 1 to 11 carbon atoms, aryl, amino lower alkylene, or a lower alkylene phosphonic acid group;
  $R_2$ indicates the phosphonic acid group;
  $R_3$ indicates an alkylene sulfonic acid group of the formula $C_nH_{2n}SO_3H$;
  $R_4$ indicates hydrogen or an alkylene sulfonic acid group of the formula $C_nH_{2n}SO_3H$; and
  n indicates one of the numerals 1 to 11;
and the alkali metal salts of said phosphonic acids.

2. The N-sulfo alkane amino alkane sulfonic acid of claim 1, in which
  $R_1$ is hydrogen,
  $R_2$ is the phosphonic acid group;
  $R_3$ is the sulfo ethane group; and
  $R_4$ is hydrogen,
said acid being N-sulfo ethane amino methane diphosphonic acid.

3. The N-sulfo alkane amino alkane phosphonic acid of claim 1, in which
  $R_1$ is hydrogen;
  $R_2$ is the phosphonic acid group;
  $R_3$ and $R_4$ are the sulfo ethane group,
said acid being the N,N-bis-sulfo ethane amino methane diphosphonic acid.

4. The N-sulfo alkane amino alkane phosphonic acid of claim 1, in which
  $R_1$ is methyl;
  $R_2$ is the phosphonic acid group;
  $R_3$ is the sulfo ethane group; and
  $R_4$ is hydrogen,
said acid being the N-sulfo ethane 1-amino ethane-1,1-diphosphonic acid.

5. The N-sulfo alkane amino alkane phosphonic acid of claim 1, in which
  $R_1$ is methyl;
  $R_2$ is the phosphonic acid group;
  $R_3$ is the sulfo butane group; and
  $R_4$ is hydrogen,
said acid being the N-sulfo butane 1-amino ethane-1,1-diphosphonic acid.

6. The N-sulfo alkane amino alkane phosphonic acid of claim 1, in which
  $R_1$ is methyl;
  $R_2$ is the phosphonic acid group;
  $R_3$ is the sulfo octane group;
  $R_4$ is hydrogen,
said acid being the N-sulfo octane 1-amino ethane-1,1-diphosphonic acid.

7. The N-sulfo alkane amino alkane phosphonic acid of claim 1, in which
  $R_1$ is the ethylene phosphonic acid group;
  $R_2$ is the phosphonic acid group;
  $R_3$ is the sulfo ethane group; and
  $R_4$ is hydrogen,
said acid being the N-sulfo ethane-1-aminopropane-1,1,3-triphosphonic acid.

8. The N-sulfo alkane amino alkane phosphonic acid of claim 1, in which
  $R_1$ is ethyl;
  $R_2$ is the phosphonic acid group;
  $R_3$ is the sulfo propane group; and
  $R_4$ is hydrogen,
said acid being the N-sulfo propane-1-amino propane-1,1-diphosphonic acid.

9. The N-sulfo alkane amino alkane phosphonic acid of claim 1, in which
  $R_1$ is phenyl,
  $R_2$ is the phosphonic acid group;
  $R_3$ is the sulfo ethane group; and
  $R_4$ is hydrogen,
said acid being the N-sulfo ethane phenyl amino methane diphosphonic acid.

10. The sulfo alkane amino alkane phosphonic acid of the formula as given in claim 1, in which formula
  $R_1$ indicates hydrogen, methyl, ethyl, amino methylene, phenyl, or the ethylene phosphonic acid group;
  $R_2$ indicates the phosphonic acid group;
  $R_3$ indicates an alkylene sulfonic acid group of the formula $C_nH_{2n}SO_3H$,
  $R_4$ indicates hydrogen or an alkylene sulfonic acid group of the formula $C_nH_{2n}SO_3H$; and
  n indicates one of the numerals 1 to 11.

* * * * *

UNITED STATES PATENT AND TRADEMARK OFFICE
CERTIFICATE OF CORRECTION

PATENT NO. : 4,216,163
DATED : August 5, 1980
INVENTOR(S) : Klaus Sommer and Hermann Weber It is certified that error appears in the above–identified patent and that said Letters Patent are hereby corrected as shown below:

Column 5, between lines 27 and 28, insert --with a cation exchange agent in order to produce the free--.

Column 7, line 12, change "phosphoric" to --phosphonic--.

Signed and Sealed this

Third Day of February 1981

[SEAL]

Attest:

RENE D. TEGTMEYER

Attesting Officer   Acting Commissioner of Patents and Trademarks